United States Patent
Honda et al.

(10) Patent No.: US 9,265,970 B2
(45) Date of Patent: Feb. 23, 2016

(54) PARTICLE BEAM IRRADIATION SYSTEM

(75) Inventors: Taizo Honda, Tokyo (JP); Masahiro Ikeda, Tokyo (JP)

(73) Assignee: MITSUBISHI ELECTRIC CORPORATION, Chiyoda-Ku, Tokyo (JP)

(*) Notice: Subject to any disclaimer, the term of this patent is extended or adjusted under 35 U.S.C. 154(b) by 180 days.

(21) Appl. No.: 13/393,418

(22) PCT Filed: Mar. 2, 2011

(86) PCT No.: PCT/JP2011/054768
§ 371 (c)(1),
(2), (4) Date: Feb. 29, 2012

(87) PCT Pub. No.: WO2012/117538
PCT Pub. Date: Sep. 7, 2012

(65) Prior Publication Data
US 2012/0223247 A1  Sep. 6, 2012

(51) Int. Cl.
*H01J 3/26* (2006.01)
*A61N 5/10* (2006.01)

(52) U.S. Cl.
CPC ............ *A61N 5/1043* (2013.01); *A61N 5/1067* (2013.01); *A61N 5/1068* (2013.01); *A61N 2005/1059* (2013.01); *A61N 2005/1087* (2013.01); *A61N 2005/1095* (2013.01)

(58) Field of Classification Search
CPC ............ A61N 2005/1059; A61N 2005/1087; A61N 5/1043; A61N 5/1067; A61N 5/1068; A61N 2005/1095
USPC ........ 250/492.2, 396 R, 492.23, 398, 492.21, 250/492.3, 492.1
See application file for complete search history.

(56) References Cited

U.S. PATENT DOCUMENTS 6,087,672 A * 7/2000 Matsuda .............. A61N 5/1042
250/492.3
7,385,203 B2 * 6/2008 Nakayama ............... H05H 7/10
250/400

(Continued)

FOREIGN PATENT DOCUMENTS

EP   1 371 390 A1   12/2003
EP   2 146 354 A1   1/2010

(Continued)

OTHER PUBLICATIONS

International Search Report (PCT/ISA/210) issued on May 24, 2011, by Japanese Patent Office as the International Searching Authority for International Application No. PCT/JP2011/054768 (in Japanese—4 pages).

(Continued)

*Primary Examiner* — Wyatt Stoffa
(74) *Attorney, Agent, or Firm* — Buchanan Ingersoll & Rooney PC

(57) ABSTRACT

A particle beam irradiation system comprises deflection electromagnets which scan by deflecting the particle beam in two dimensions in the lateral direction which is perpendicular to an irradiation direction of the particle beam, and an energy width expanding device through which the particle beam passes so as to expand an energy width of the particle beam and form a SOBP in a depth direction of the irradiation target, that is, in an irradiation direction of the particle beam, wherein the energy width expanding device is configured to form the SOBP in the depth direction along whole irradiation area in the depth direction of the irradiation target, and the deflection electromagnets are controlled so as for an irradiation spot which is formed in the irradiation target by the particle beam to move stepwise along whole irradiation area in the lateral direction of the irradiation target.

3 Claims, 15 Drawing Sheets

(56) References Cited

U.S. PATENT DOCUMENTS

| | | | | |
|---|---|---|---|---|
| 7,525,104 | B2* | 4/2009 | Harada | 250/396 R |
| 8,232,536 | B2* | 7/2012 | Harada | A61N 5/1042 250/396 R |
| 8,637,837 | B2* | 1/2014 | Natori | A61N 5/1043 250/492.1 |
| 8,704,197 | B2* | 4/2014 | Gemmel | H05H 7/00 250/396 R |
| 2004/0000650 | A1 | 1/2004 | Yanagisawa et al. | |
| 2004/0056212 | A1 | 3/2004 | Yanagisawa et al. | |
| 2004/0149934 | A1 | 8/2004 | Yanagisawa et al. | |
| 2005/0099145 | A1* | 5/2005 | Nishiuchi | H05H 13/04 315/500 |
| 2005/0145804 | A1 | 7/2005 | Yanagisawa et al. | |
| 2006/0097204 | A1 | 5/2006 | Yanagisawa et al. | |
| 2006/0273264 | A1* | 12/2006 | Nakayama | H05H 7/10 250/492.3 |
| 2008/0067401 | A1 | 3/2008 | Harada | |
| 2010/0051833 | A1* | 3/2010 | Guertin | H05H 7/12 250/515.1 |
| 2010/0187435 | A1* | 7/2010 | Iseki | A61N 5/1043 250/398 |
| 2010/0207042 | A1* | 8/2010 | Harada | A61N 5/1049 250/492.3 |
| 2010/0243911 | A1* | 9/2010 | Fujii | A61N 5/1044 250/400 |
| 2010/0288946 | A1* | 11/2010 | Honda | A61N 5/10 250/492.3 |
| 2012/0008745 | A1* | 1/2012 | Stahl | A61N 5/1047 378/65 |

FOREIGN PATENT DOCUMENTS

| | | |
|---|---|---|
| JP | 7-148277 A | 6/1995 |
| JP | 11-019235 A | 1/1999 |
| JP | 2006-087649 A | 4/2006 |
| JP | 2008-161716 A | 7/2008 |
| JP | 2009-039219 A | 2/2009 |
| JP | 2009-066106 A | 4/2009 |
| JP | 2009/268940 A | 11/2009 |
| JP | 2009-268940 A | 11/2009 |
| JP | 2010-253000 A | 11/2010 |
| WF | WO 2006/082651 A1 | 8/2006 |
| WO | 2009/035080 A1 | 3/2009 |
| WO | WO 2010006736 A1 * | 1/2010 |

OTHER PUBLICATIONS

Written Opinion (PCT/ISA/237) issued on May 24, 2011, by Japanese Patent Office as the International Searching Authority for International Application No. PCT/JP2011/054768 (in Japanese—6 pages).

Japanese Office Action dated Apr. 2, 2013, issued in corresponding Japanese Patent Application No. 2011-549088, and a Partial English Translation of the Office Action. (6 pgs.).

Taiwanese Office Action dated Oct. 9, 2013, issued in the corresponding Taiwanese Patent Application No. 100135456, and a partial English Translation of the Office Action thereof. (17 pgs.).

Extended European Search Report issued Jun. 23, 2014, by the European Patent Office in corresponding European Patent Application No. 11859722.8-1652. (6 pages).

Office Action issued on Jul. 1, 2014, by the Japanese Patent Office in corresponding Japanese Patent Application No. 2013-216942 and partial English translation. (11 pages).

First Chinese Office Action issued May 6, 2015 in corresponding Chinese Patent Application No. 2011800685766, with full English translation (12 pages).

* cited by examiner

PARTICLE BEAM IRRADIATION SYSTEM

TECHNICAL FIELD

This invention relates to a particle beam irradiation system in which particle beam is applied such as performing a treatment of cancer by radiating a particle beam.

BACKGROUND ART

The treatment of a cancer is one of applications of radiation. Recently, a particle beam treatment in which a heavy particle beam such as a proton beam or a carbon beam is irradiated onto the cancer cell has been attracted attention. First of all, the characteristic of a particle beam irradiation in which a particle beam is irradiated to kill a cancer cell will be described. In a case where various kinds of irradiation beams are irradiated onto a human body, the dose distribution of the irradiation beam in the human body changes as shown in FIG. 15. As shown in FIG. 15, among various kinds of irradiations, a photon beam such as an X-ray or a gamma ray, has a relative dose which becomes maximum in a portion close to the surface of the body, and is decreased as the depth from the surface of the body is increased. On the other hand, a particle beam, such as a proton beam or a carbon beam, has a relative dose which has a peak value at a position where the beam stops at a deep portion from the surface of the body, that is, immediately before the range of the particle beam. This peak value is called the Bragg Peak (BP).

Particle beam cancer treatment is such that this Bragg peak BP is irradiated to a tumor formed in a human organ and the treatment of the cancer is performed. In addition to the cancer, it can also be used for a case where a deep portion of a body is treated. A region to be treated, including a tumor, is generally called an irradiation target. The position of the Bragg peak BP is determined by the energy of an irradiated particle beam, and as the energy of the particle beam becomes higher, the Bragg peak BP is formed at a deeper position. In the particle beam treatment, it is required to provide uniform distribution of dose of a particle beam in whole region of an irradiation target. In order to give the Bragg peak BP to the whole region of the irradiation target, "spread of the irradiation volume" of the particle beam is performed.

This "spread of the irradiation volume" is performed in three directions of an X-axis, a Y-axis and a Z axis perpendicular to each other. When an irradiation direction of a particle beam is set to be a direction of the Z-axis, "spread of the irradiation volume" is first performed so as to spread the irradiation field in the X-axis and Y-axis directions, and since the irradiation field spread is performed in a lateral direction perpendicular to a depth direction, it is generally called the irradiation field spread. The second "spread of irradiation volume" is performed in the Z-axis, and it is called the irradiation volume spread in a depth direction.

The irradiation volume spread in a depth direction is performed to spread the Bragg peak BP in an irradiation direction of a particle beam to a depth direction since the width of the Bragg peak BP in an irradiation direction of a particle beam is narrow as compared with the extent of an irradiation target in a depth direction. On the other hand, the irradiation field spread in a lateral direction is performed to spread the irradiation field in the Bragg peak BP in a direction perpendicular to an irradiation direction since the diameter of a particle beam, which is accelerated by an accelerator generally, is smaller than the size of an irradiation target in a direction perpendicular to an irradiation direction. With respect to the irradiation volume spread in a depth direction and the irradiation field spread in a lateral direction, various kinds of methods have been proposed so far. Recently, Scanning Irradiation has attracted attention.

In Scanning Irradiation, as an irradiation field spread method in a lateral direction, there is a method in which a deflection electromagnet provided at the upstream portion of a particle beam irradiation part of a particle beam treatment device is used to scan a particle beam in the XY plane, and an irradiation position of the particle beam is moved with the lapse of time to obtain a wide irradiation field. In this method, a uniform dose distribution can be obtained by suitably overlapping adjacent irradiation spots of pencil beams having a small diameter. Scanning methods of a pencil beam include a raster method of performing scanning continuously with respect to time, a spot method of performing a step-like scanning with respect to time and a method combining the raster method and the spot method.

As the irradiation volume spread method in the depth direction, there is a method in which the energy of a particle beam itself which is irradiated from a particle beam treatment device is controlled. In this method, the energy of a particle beam is controlled by changing the acceleration energy of an accelerator which accelerates the particle beam, or the energy of a particle beam is changed by inserting a tool called a range shifter so as to cross the particle beam. There is also a method in which both the control by the accelerator and the range filter are used.

In the irradiation volume spread method in the depth direction, a particle beam is made to have the energy of specified intensity, after one of irradiation layers of an irradiation target volume is irradiated with the Bragg peak BP, the energy of the particle beam is changed, and next irradiation layer of the irradiation target volume is irradiated with the Bragg peak BP. Such operation is repeated plural times so as for plural irradiation layers to be irradiated with the Bragg peak BP of the particle beam. Consequently, the Spread-out Bragg peak SOBP having a desired width in a beam irradiation direction can be obtained. (For example, Patent Document 1)

A particle beam irradiation method which is made by combining the irradiation field spread method in a lateral direction and the irradiation volume spread method in a depth direction is called Scanning Irradiation.

Further, a method in which irradiation is performed at the same spot position for plural times with time-wise dividing at each irradiation layer so as to compensate the deviation of irradiation caused by moving of a position of affected site due to a patient's breathing, is proposed (For example, Patent Document 2, FIG. 11). Further, in the Patent Document 2, a technique, for controlling the irradiation dose by synchronizing with a breathing phase in consideration of the moving of an affected site caused by breathing, is also proposed.

PRIOR ART REFERENCES

Patent Document

Patent Document 1: Patent Application Laid-Open No. 2006-87649
Patent Document 2: International Publication of WO2006/082651 (FIG. 11)

DISCLOSURE OF THE INVENTION

Problems to be Solved by the Invention

In the above-mentioned conventional scanning irradiation method, it is required to change energy of a particle beam for plural times to perform irradiation. Therefore, it takes time to change the energy and it is difficult to shorten the irradiation time.

In order to solve the above-mentioned problem, this invention aims to provide a dose distribution with higher accuracy at higher speed in a particle beam irradiation system according to a scanning irradiation.

Means for Solving the Problems

A particle beam irradiation system according to this invention comprises deflection electromagnets for scanning which scan by deflecting the particle beam in two dimensions in the lateral direction which is perpendicular to an irradiation direction of the particle beam, and an energy width expanding device through which the particle beam passes so as to expand an energy width of the particle beam and form a SOBP in a depth direction of the irradiation target, that is, in an irradiation direction of the particle beam, wherein the energy width expanding device is configured to form the SOBP in the depth direction along whole irradiation area in the depth direction of the irradiation target, and the deflection electromagnets for scanning are controlled so as for an irradiation spot which is formed in the irradiation target by the particle beam to move stepwise along whole irradiation area in the lateral direction of the irradiation target.

Advantage of the Invention

In scanning irradiation in which an irradiation target is irradiated by moving an irradiation spot, which is formed by a particle beam, in a lateral direction, irradiation is performed along whole irradiation area in a depth direction of an irradiation target without changing the energy. Consequently, this invention can provide a particle beam irradiation system in which irradiation can be completed in a short time, and a dose distribution with higher accuracy can be given to an irradiation target.

EMBODIMENTS FOR CARRYING OUT THE INVENTION

Embodiment 1

Figure 2:
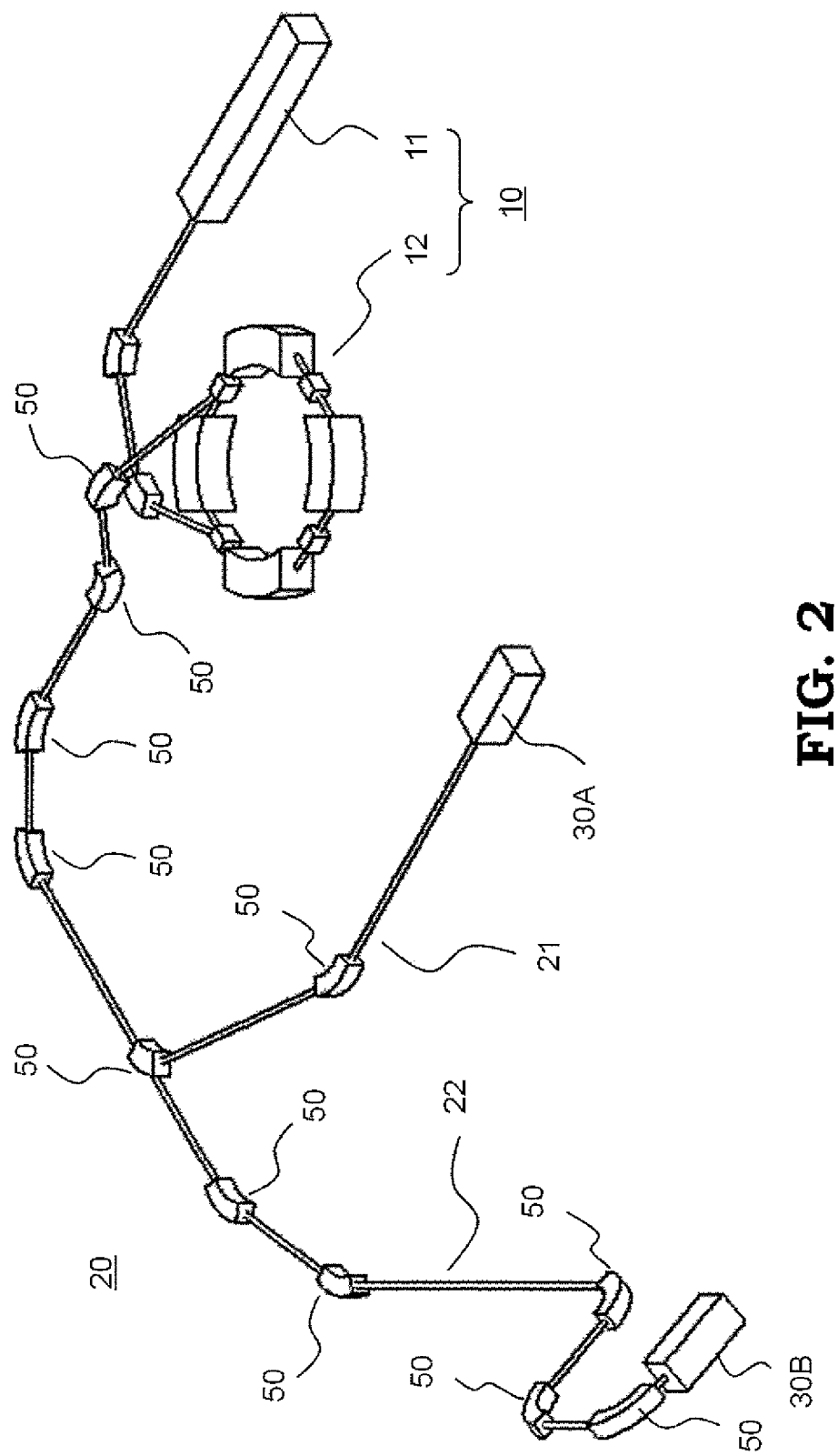
FIG. 2 is a bird's-eye view showing an outline of configuration of whole of a particle beam irradiation system according to EMBODIMENT 1 of the present invention.
Figure 3:
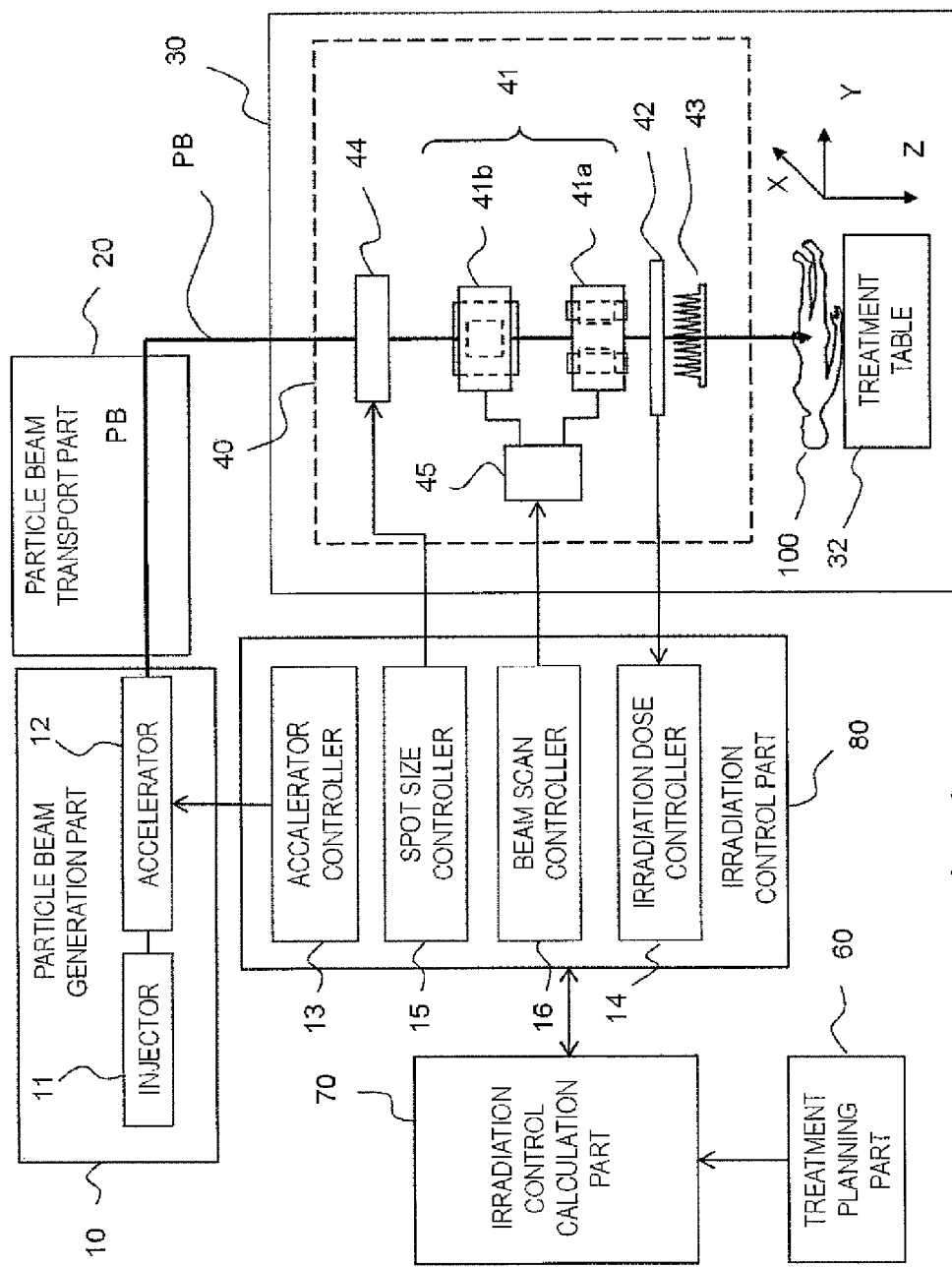
FIG. 3 is a block diagram showing an outline of configuration of a particle beam irradiation system according to EMBODIMENT 1 of the present invention.

FIG. 2 is a bird's-eye view showing an outline of configuration of whole of a particle beam irradiation system according to EMBODIMENT 1 of the present invention and FIG. 3 is a block diagram showing an outline of configuration of a particle beam irradiation system according to EMBODIMENT 1 in which a control device, etc. is added to whole configuration shown in the bird's-eye view of FIG. 2. As shown in FIGS. 2 and 3, the particle beam irradiation system according to EMBODIMENT 1 includes a particle beam generation part 10, a particle beam transport part 20, and two particle beam irradiation parts 30A and 30B. FIG. 2 shows a particle beam irradiation system having two particle beam irradiation parts as a representative example, however, a particle beam irradiation system having one particle beam irradiation part or three or more particle beam irradiation parts may be acceptable. In FIG. 3, for simplification, only one particle beam irradiation part is shown as a particle beam irradiation part 30. For reasons of application of radiation safety management and the like, the particle beam generation part 10, and the particle beam irradiation parts 30A and 30B are installed in individual shielded rooms. The particle beam transport part 20 connects the particle beam generation part 10 to the particle beam irradiation parts 30A and 30B. The particle beam transport part 20 includes particle beam transport passages 21 and 22 to transport a particle beam generated in the particle beam generation part 10 to the particle beam irradiation parts 30A and 30B, respectively. The particle beam transport part 20 has bending electromagnets 50 for changing the direction of a particle beam and is constructed so as for a particle beam to pass through a vacuum duct. The particle beam irradiation parts 30A and 30B are configured such that a target site of a patient is irradiated with a particle beam PB. Hereinafter, the particle beam irradiation parts 30A and 30B will be described as the particle beam irradiation part 30.

The particle beam generation part 10 includes an injector 11 and an accelerator 12. The injector 11 generates a particle beam having large mass such as a proton beam or a carbon beam. The accelerator 12 accelerates a particle beam generated by the injector 11, and forms a particle beam PB. The accelerator 12 is controlled by a signal which is transmitted from an accelerator controller 13 which is provided in an irradiation control part 80. The accelerator controller 13 supplies an energy control signal to the accelerator 12 and sets an acceleration energy so as to set an energy of a particle beam PB which is emitted from the accelerator 12, or so as to control the time when a particle beam PB is extracted and the intensity of a particle beam PB.

The particle beam irradiation part 30 constitutes a treatment room. The particle beam irradiation part 30 includes an irradiation nozzle 40 and a treatment table 32. The treatment table 32 is used for keeping a patient in the state of a dorsal position or a sitting position. The irradiation nozzle 40 irradiates a particle beam PB which is transported to the particle beam irradiation part 30 onto an irradiation target of a patient on the treatment table 32.

FIG. 3 shows the specific configuration of the irradiation nozzle 40 of the particle beam irradiation part 30. The irradiation nozzle 40 shown in FIG. 3 has a beam diameter changer 44 for changing a beam diameter of a particle beam PB. As a beam diameter changer, various kinds of changers may be used. The beam diameter changer includes a changer in which a quadrupole electromagnet is used, and a changer in which a thin scatterer is used and a beam diameter in an irradiation target can be changed by changing a thickness of the scatterer. Further, in a case where the beam diameter is not required to change or select, the beam diameter changer 44 may be omitted. The irradiation nozzle 40 comprises deflection electromagnets for scanning 41$a$ and 41$b$ (both of the deflection electromagnets for scanning 41$a$ and 41$b$ may be referred as a deflection electromagnet for scanning 41) which scan a particle beam PB, after whose beam diameter is changed, in the lateral direction, that is, in an X phase and a Y phase which are perpendicular to an irradiation direction of a particle beam PB, a driving power source of a deflection electromagnet for scanning 45 for driving the deflection electromagnet for scanning 41, a dose monitor 42 for monitoring an irradiation dose of a particle beam PB, and a ridge filter 43 which is a energy width expanding device for expanding an energy width of a particle beam. PB. In addition to the above, a particle beam irradiation system may comprise a beam position monitor, etc., however, this is not directly related to this invention, therefore, the beam position monitor, etc., will be omitted.

Figure 4:
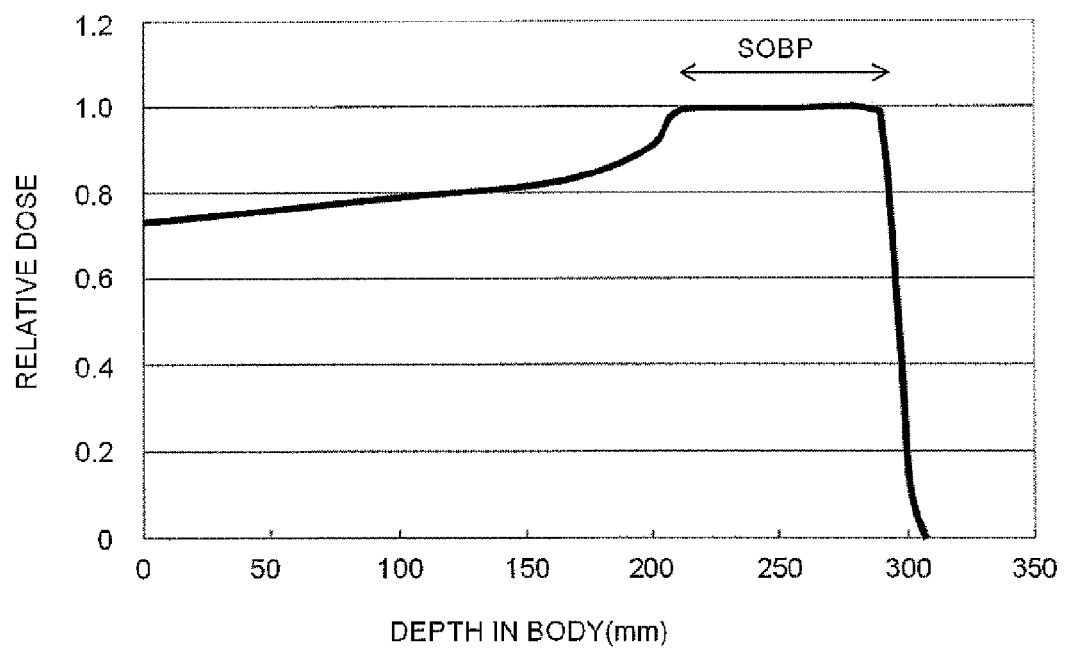
FIG. 4 is a diagrammatic view showing an example of SOBP which is expanded by a particle beam irradiation system according to EMBODIMENT 1 of the present invention.

The ridge filter 43 decreases energy of a particle beam which passes through it, however, the filter is configured such that a thickness of the filter is different depending on a position. Therefore, as a whole, a particle beam which has passed through the filter has an energy width which is larger than that of a particle beam before which passes through the filter. Consequently, when inside of a body is irradiated with a particle beam which has passed through the ridge filter 43, a position of the Bragg Peak (BP), that is, the range of a particle beam is spread. An example of a Spread-out Bragg Peak (SOBP) will be shown in FIG. 4. In FIG. 4, the SOBP has the length of approximately 10 cm. When a ridge filter which forms the SOBP shown in FIG. 4 is used, an irradiation target having a width of 10 cm in a depth direction can be irradiated.

Next, an operation of a particle beam irradiation system shown in FIG. 3 will be explained. First, in a treatment planning part 60, an irradiation dose distribution for each patient is determined and the data are stored. In an irradiation control calculation part 70, based on the data of an irradiation dose distribution, an irradiation dose at each irradiation spot is determined and its data are outputted to an irradiation dose controller 14 of the irradiation control part 80. Further, in the irradiation control calculation part 70, energy of a particle beam which should be extracted by the accelerator 12 and a spot size will be determined and its data will be outputted to the accelerator controller 13 and a spot size controller 15. By performing the above-mentioned, preparation before irradiation will be completed.

Figure 1:
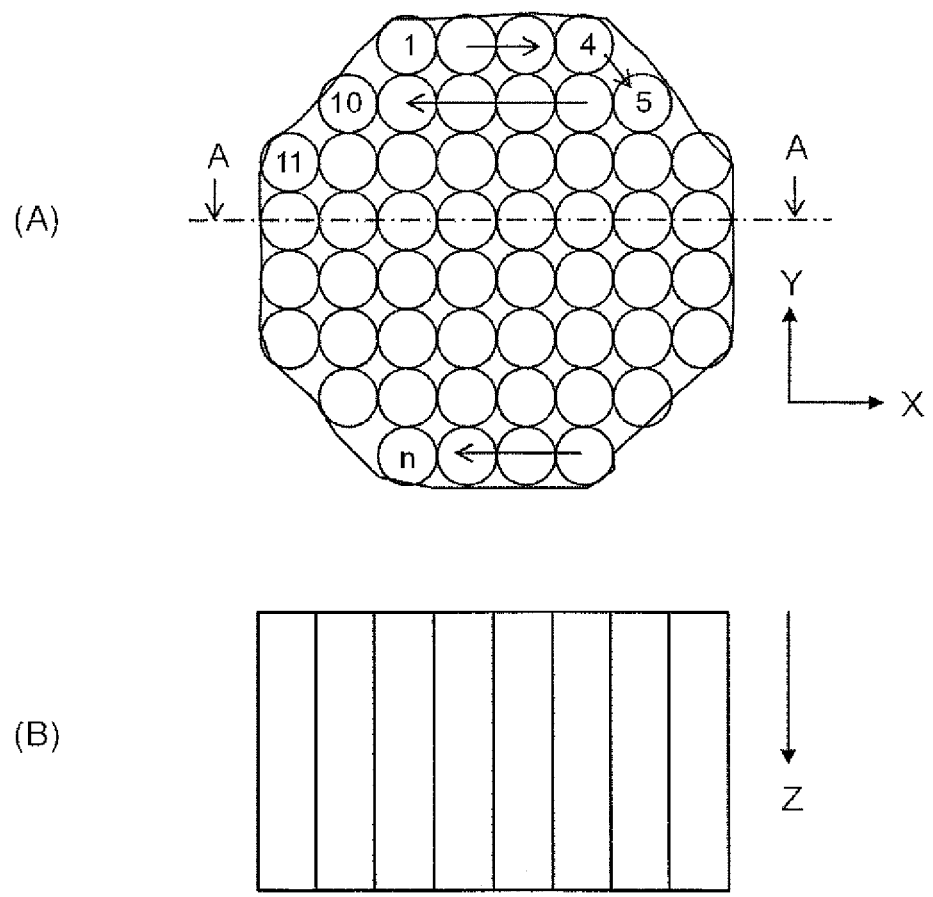
FIG. 1 is a diagram for describing an irradiation area of a particle beam irradiation system according to EMBODIMENT 1 of the present invention.
Figure 5:
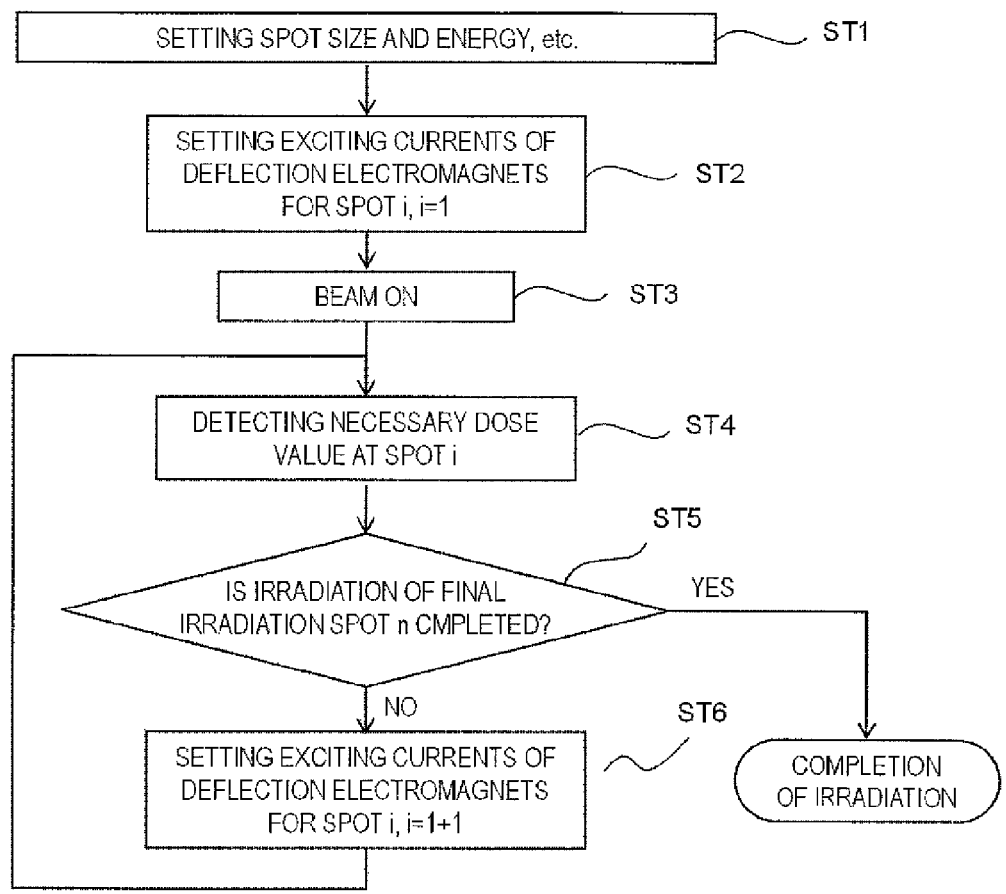
FIG. 5 is a flow chart showing steps of a particle beam irradiation system when a particle beam is radiated according to EMBODIMENT 1 of the present invention.

Next, FIG. 1 shows an image of an irradiation area when an irradiation target is actually irradiated with a particle beam. In FIG. 1 (A), a circle shows each irradiation spot, and numeral in a circle shows the order of scanning. Further, FIG. 1 (B) is a cross sectional view taken along the line A-A of FIG. 1 (A). FIG. 5 is a flow chart showing steps of a particle beam irradiation system when a particle beam is radiated. First, the accelerator 12 and the beam diameter changer 44 are set through the irradiation control part 80 so as for an energy and a spot size which are determined by the irradiation control calculation part 70 in the preparation stage to be a determined value (ST1). Next, in order to radiate a particle beam PB to a position of an irradiation spot 1, the driving power source of a deflection electromagnet for scanning 45 is controlled by a beam scan controller 16 so as to set an exciting current of the deflection electromagnet for scanning 41 (ST2). After setting of the exciting electric current is completed, a particle beam is extracted from the accelerator 12 so as to start irradiation (ST3). When an irradiation is started, an irradiation dose is counted by the dose monitor 42. A dose count value is transmitted to the irradiation dose controller 14.

In the irradiation dose controller 14, a necessary irradiation dose value at each irradiation spot is received from the irradiation control calculation part 70. When a dose value at every irradiation spot reaches the necessary irradiation dose value, a radiation dosage termination signal is transmitted to the irradiation control calculation part 70 (ST4). When a dose at an irradiation spot reaches a predetermined value, the irradiation control calculation part 70 transmits a command to the beam scan controller 16 so as to move a particle beam to next irradiation spot, and to set an exciting electric current of the deflection electromagnet for scanning 41 to be an exciting electric current corresponding to the next irradiation spot (ST6). The above-mentioned operation will be repeated until an irradiation at a final irradiation spot (an irradiation spot which is indicated by n in FIG. 1) is completed.

FIG. 1 shows a area in which irradiation is performed according to the above-mentioned steps. An irradiated area in a lateral direction, that is, in an XY direction is a whole area which is formed by moving an irradiation spot stepwise by the deflection electromagnets for scanning 41, and an irradiated area in a depth direction, that is in a z direction is a area corresponding to Bragg Peak which is spread by an energy of a particle beam which is spread by the ridge filter 43. When a general ridge filter is used, an energy width of a particle beam is the same in an XY whole area. Therefore, in a z direction, an area having a given width is an irradiation area. Consequently, at every irradiation spot, a columnar area is an irradiation area, and whole irradiation area which is made of whole irradiation spots becomes a cylindrical shape area. In a case where a shape of affected site is similar to a rolled-shape, by setting an energy of a particle beam which is extracted from the accelerator 12 and the ridge filter 43 so as to form a spread-out Bragg Peak corresponding to a depth of an affected site, irradiation can be completed without changing energy. In conventional spot scanning irradiation, by successively changing an energy of a particle beam to be radiated, whole area is irradiated by forming plural layers of irradiation in a depth direction. According to the above-mentioned method, it is necessary to successively change an energy. In order to change energy, it is necessary to change a parameter of the accelerator 12 or to change a parameter of a range shifter which is inserted after a particle beam is extracted from the accelerator 12. Consequently, it takes time. On the other hand, according to this invention, it is not necessary to change energy of a particle beam, and whole area can be irradiated only by one scanning in an XY direction. Consequently, irradiation time can be shortened; as a result, a burden on a patient can be relieved.

Embodiment 2

Figure 6:
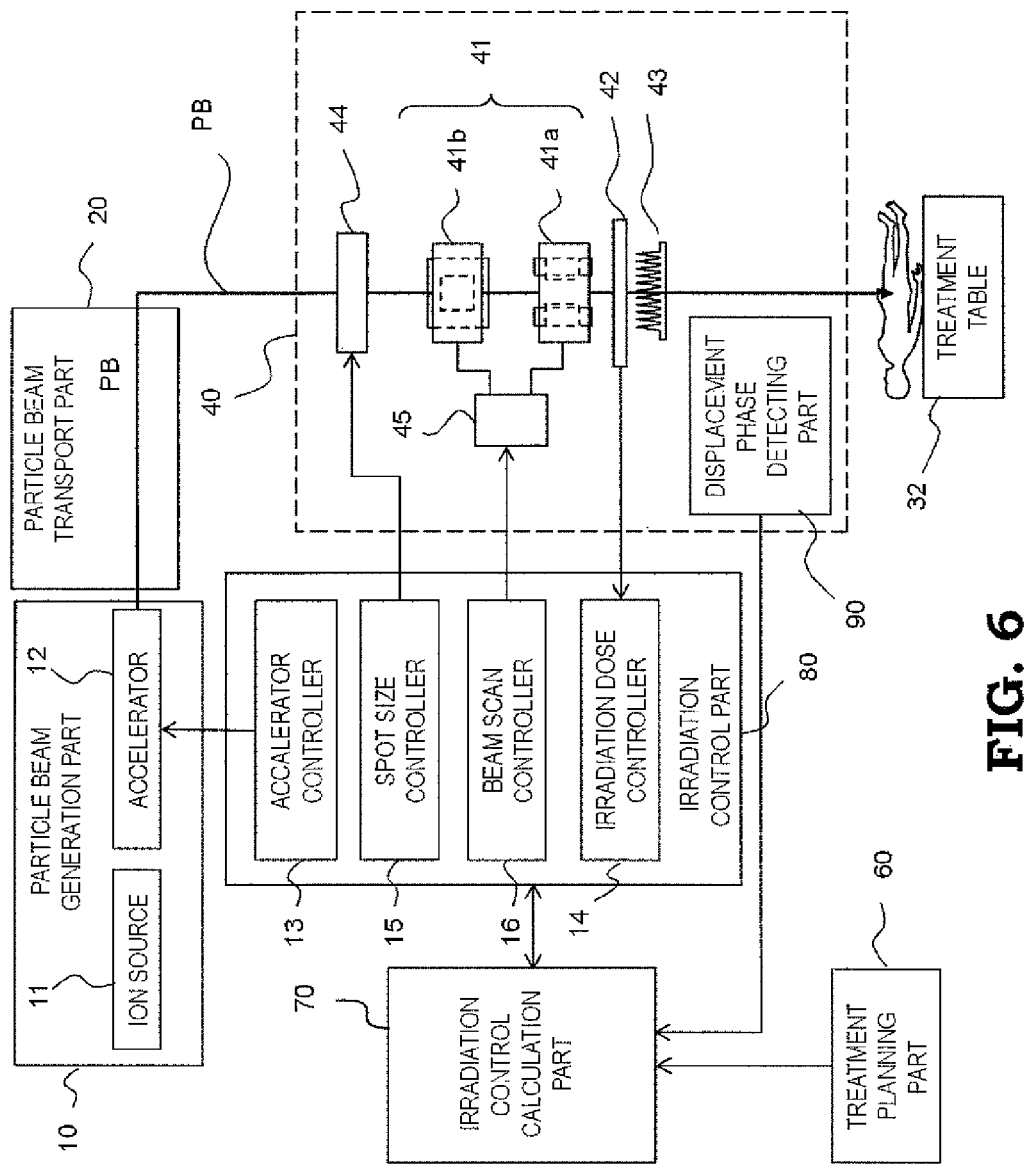
FIG. 6 is a block diagram showing an outline of configuration of a particle beam irradiation system according to EMBODIMENT 2 of the present invention.

FIG. 6 is a block diagram showing an outline of configuration of a particle beam irradiation system according to EMBODIMENT 2 of the present invention. In FIG. 6, the same symbol as that of FIG. 3 indicates the same part or a corresponding part. In EMBODIMENT 2, as shown in FIG. 6, a displacement phase detecting part 90 is provided, and a signal of displacement of a position of an affected site which is detected by the displacement phase detecting part 90 is outputted to an irradiation control calculation part 70. In the displacement phase detecting part 90, breathing of a patient is measured or a position of an irradiation target is detected. Based on the breathing measurement or the detection of a position of an irradiation target, a position of an affected site is determined. In the irradiation control calculation part 70, an irradiation control part 80 is controlled so as to irradiate a particle beam in synchronization with the phase of movement period of an affected site which is determined. Since a position of an irradiation target is changed by breathing of a patient, etc., an irradiation position of a particle beam is changed. Consequently, irradiation accuracy is decreased. At the time of exhaling, etc., the degree of change of a position of an irradiation target is small. Therefore, when an irradiation is performed during the period of exhaling, irradiation with high accuracy can be performed. In EMBODIMENT 2, further, irradiation is performed along an XY whole irradiation area during a period of one exhalation. By performing the above-mentioned, irradiation with extremely high accuracy can be performed.

Figure 7:
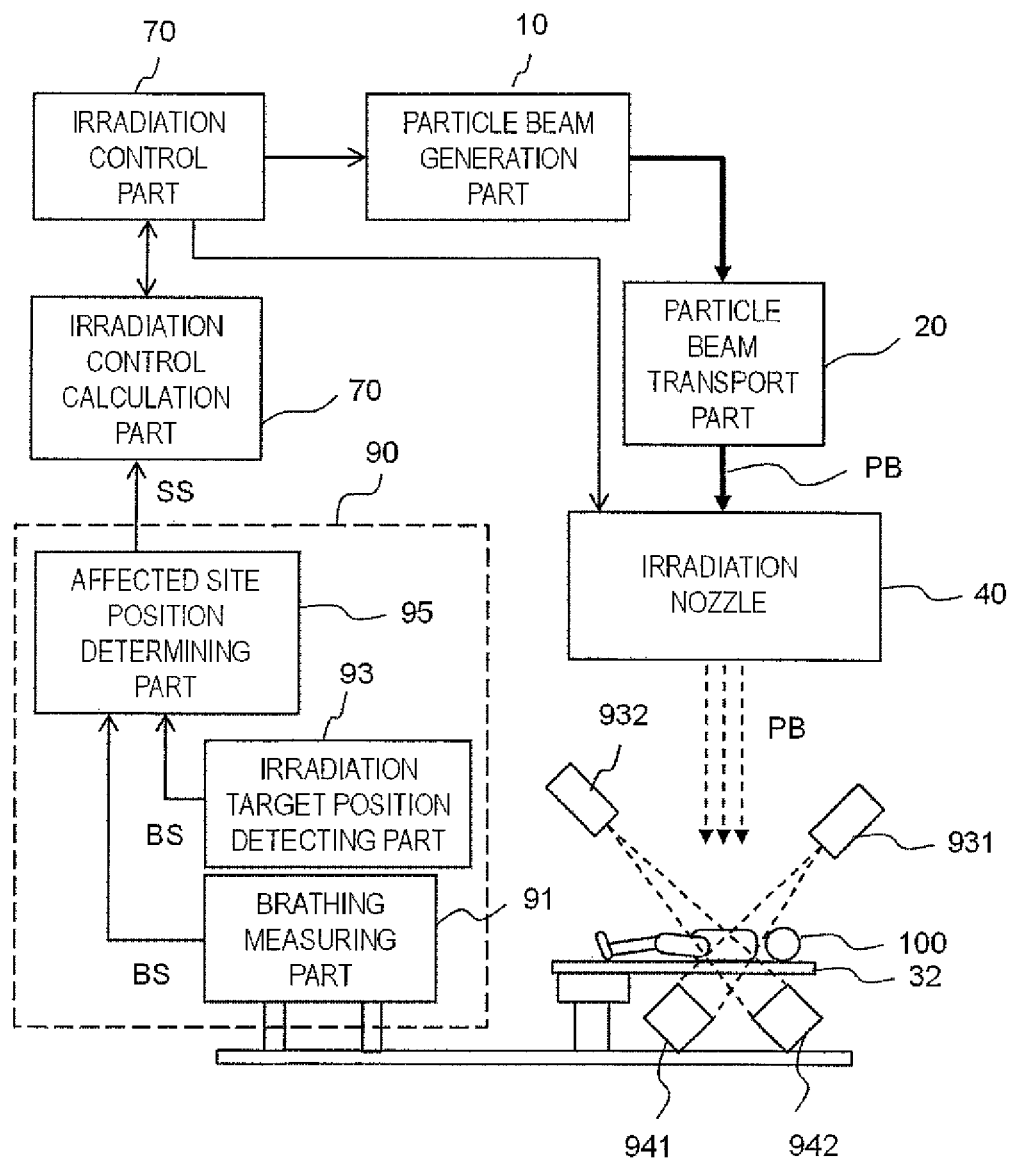
FIG. 7 is a block diagram showing an example of configuration of displacement phase detecting part of a particle beam irradiation system according to EMBODIMENT 2 of the present invention.

FIG. 7 is a block diagram showing the details of an example of the displacement phase detecting part 90. A breathing measuring part 91 measures breathing of a patient 100 so as to output a breathing signal BS, and as a breathing measuring part 91, a breathing measuring part which is used in conventional particle beam irradiation system or an X-ray CT may be used. In the breathing measuring part 91, a method in which a light-emitting diode (LED) is attached to an abdomen or a chest of a patient 100, and breathing is measured by displacement of a light-emitting position of the light-emitting diode (LED); a method in which displacement of a body is measured by a laser beam using a reflection device; a method in which an extensible resistance is attached to an abdomen of a patient so as to measure the change of its electric property, and a method in which breath of a patient 100 is directly measured can be used.

An irradiation target position detecting part 93 detects a position of an irradiation target in the patient 100 so as to output a breathing signal BS. As the irradiation target position detecting part 93, an X-ray sources 931 and 932, and an X-ray image acquisition devices 941 and 942 corresponding to the X-ray sources 931 and 932, respectively are used. The X-ray sources 931 and 932 radiate an X-ray to an irradiation target in the patient 100, and the X-ray image acquisition devices 941 and 942 acquire images of X-ray which are transmitted from the X-ray sources 931 and 932 so as to detect a position of an irradiation target. As the X-ray image acquisition devices 941 and 942, for example, an X-ray television device in which an image intensifier is used, or a device using a method in which a scintillator plate is measured by using CCD camera is used. There is a method in which a small piece of metal such as gold is implanted in advance as a marker at a strategic point corresponding to an irradiation target. By using the marker, it becomes easier to specify a position of an irradiation target.

Both of the breathing measuring part 91 and the irradiation target position detecting part 93 detect a displacement of an irradiation target caused by breathing, etc. so as to generate a breathing signal BS. Both of breathing signals from the breathing measuring part 91 and the irradiation target position detecting part 93 are inputted to an affected site position determining part 95. Based on the correlation between inspiration and expiration which is stored in the memory, the affected site position determining part 95 determines a breathing displacement in real time from a breathing signal BS which is inputted so as to output a status signal SS to the irradiation control calculation part 70.

Figure 8:
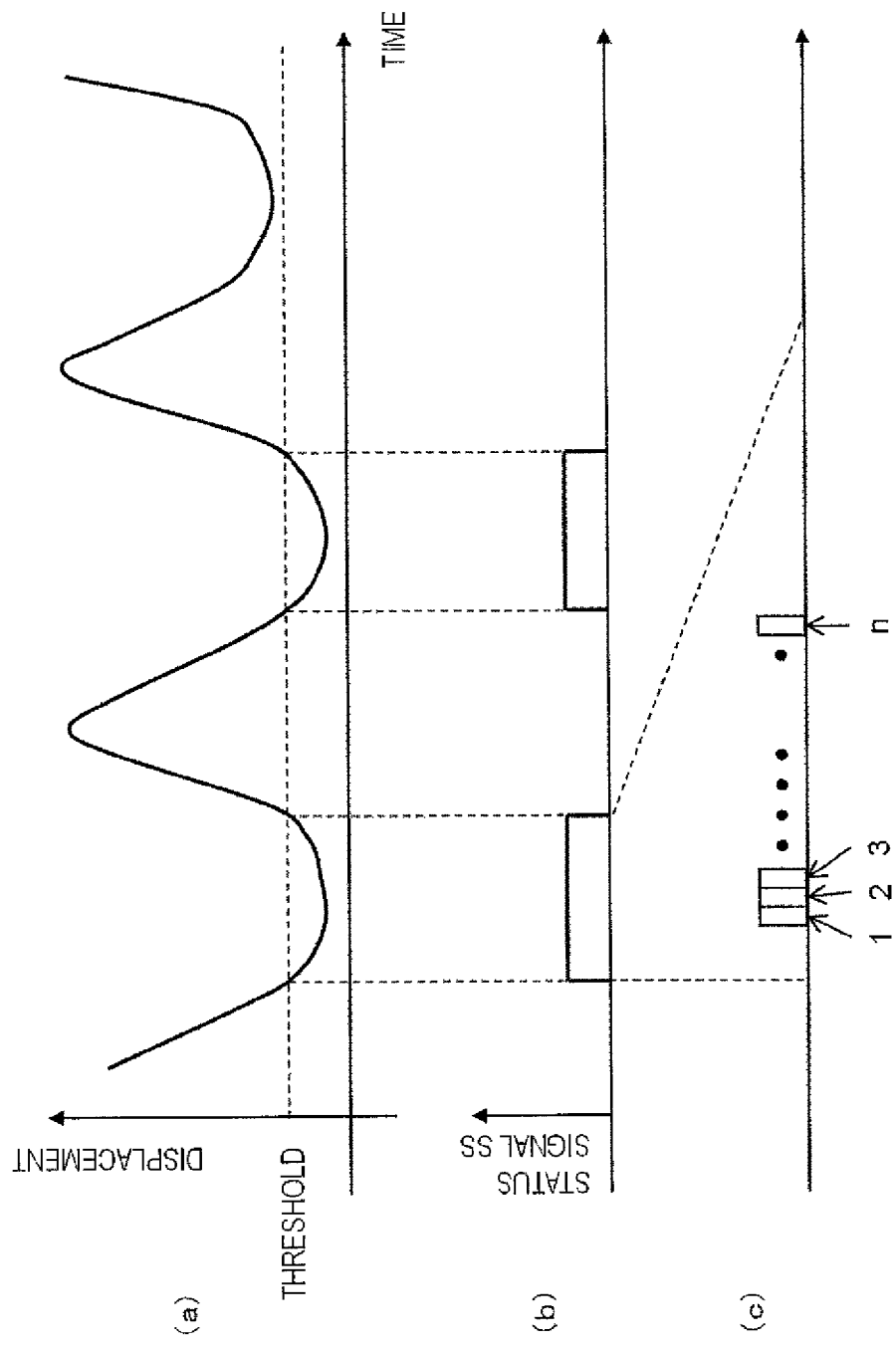
FIG. 8 is a diagrammatic view for explaining an operation of a particle beam irradiation system according to EMBODIMENT 2 of the present invention.

FIG. 8 is a diagrammatic view for explaining an outline of an operation of the displacement phase detecting part 90. FIG. 8(*a*) shows, for example, a breathing displacement of an irradiation target, and FIG. 8(*b*) shows a status signal of result which is determined based on the displacement. In FIG. 8(*a*), a lateral broken line shows a predetermined threshold, and in a case where a displacement is the predetermined threshold or less, the affected site determining part 95 outputs a status signal as shown in FIG. 8(*b*), that is a signal indicating that it is the state capable of irradiation. The irradiation control calculation part 70 controls an irradiation based on a status signal as follows.

First, prior to irradiation, movement of organ caused by breathing exercise is measured by the displacement phase detecting part 90 so as to acquire phase data of an affected site's movement period. That is, data of a status signal which are outputted by the displacement phase detecting part 90 are registered in the irradiation control calculation part 70. In the irradiation control calculation part 70, a time length of a status signal in moving an affected site (hereinafter, will be called as one gate length) is evaluated by a plurality of one gate lengths which are registered, for example. Then, an irradiation parameter for radiating whole irradiation spots in an affected site within one gate length such as irradiation dose rate (intensity) at each irradiation spot is determined by performing computing. An irradiation dose rate is obtained by dividing an irradiation dose at each irradiation spot by a permissible irradiation time. The permissible irradiation time is obtained by multiplying an irradiation time in the one gate length by irradiation rate of each spot in whole of irradiation. After an irradiation parameter is determined, irradiation is performed. However, while a status signal SS is outputted (in one gate length), irradiation is performed by using an irradiation parameter which is determined. FIG. 8(*c*) shows the image in which each irradiation spot is actually irradiated, wherein one gate length is enlarged. As shown in FIG. 8(*c*), a particle beam is radiated so as for all irradiation spots from 1 to n to be irradiated within one gate length. For example, in a case where the number of irradiation spot is evaluated to be 500, and one gate length is evaluated to be one second, when whole irradiation time is 0.5 second, for example, which is less than one gate length, irradiation parameters are determined so as for an irradiation time of one irradiation spot to be approximately 1 ms.

Depending on dose of a particle beam which can be extracted from an accelerator 12 and the size of an irradiation target, for example, in a case where, an irradiation target has a size of 5 cm×5 cm×5 cm, irradiation dose is 5GyE as a biological dose and a spot size is $\phi$2.5 mm, it is practically possible to irradiate necessary dose to all of irradiation spots, whose total number is approximately 500 and whose irradiation time is 0.5 seconds. In this case, by setting a parameter of a ridge filter 43 so as for a width of a SOBP to be 5 cm in a predetermined depth, an irradiation in a depth direction of an irradiation target can be realized without changing energy of a particle beam. Consequently, irradiation of all irradiation spots can be completed within one gate. As a result, irradiation can be performed by suppressing movement of an irradiation target during irradiation to the minimum, and irradiation with extremely high accuracy can be realized.

Further, in the above, an example in which necessary irradiation dose can be performed in whole irradiation area within one gate was described, however, necessary dose may not be necessarily irradiated within one gate. For example, in the above-mentioned example, in a case where 5GyE of irradiation dose can not be irradiated to whole irradiation area by using an amount of a particle beam which can be extracted from an accelerator by a single acceleration, 5GyE of irradiation dose can be irradiated to whole irradiation area by performing irradiation separately for a plural times. In a case where necessary irradiation dose is 5GyE, and in the irradiation control calculation part 70, it is evaluated such that 3GyE of irradiation dose can be radiated to whole irradiation area by an amount of a particle beam which is extracted from an accelerator by a single acceleration, first, whole irradiation spots are irradiated with a particle beam which is accelerated by the first acceleration in a accelerator within one gate so as to give 3GyE of irradiation dose to an irradiation target. Next, whole irradiation spots are irradiated again with a particle beam which is accelerated by the second acceleration in the accelerator within one gate after the second acceleration so as to give 2GyE of irradiation dose to the irradiation target. As above-mentioned, by using time length of two gates, 5GyE of irradiation dose in total can be given by irradiating whole irradiation spots within each gate. As above-mentioned, it is not always necessary to irradiate whole dose within one gate, but irradiation may be performed separately within a plurality of gates. However, in one gate, all irradiation spots should be irradiated, and in the following gate, all irradiation spots should be also irradiated. Since all irradiation spots are irradiated within one gate, irradiation with high accuracy can be realized at each gate. Therefore, irradiation dose with high accuracy in total can be obtained.

Embodiment 3

Figure 9:
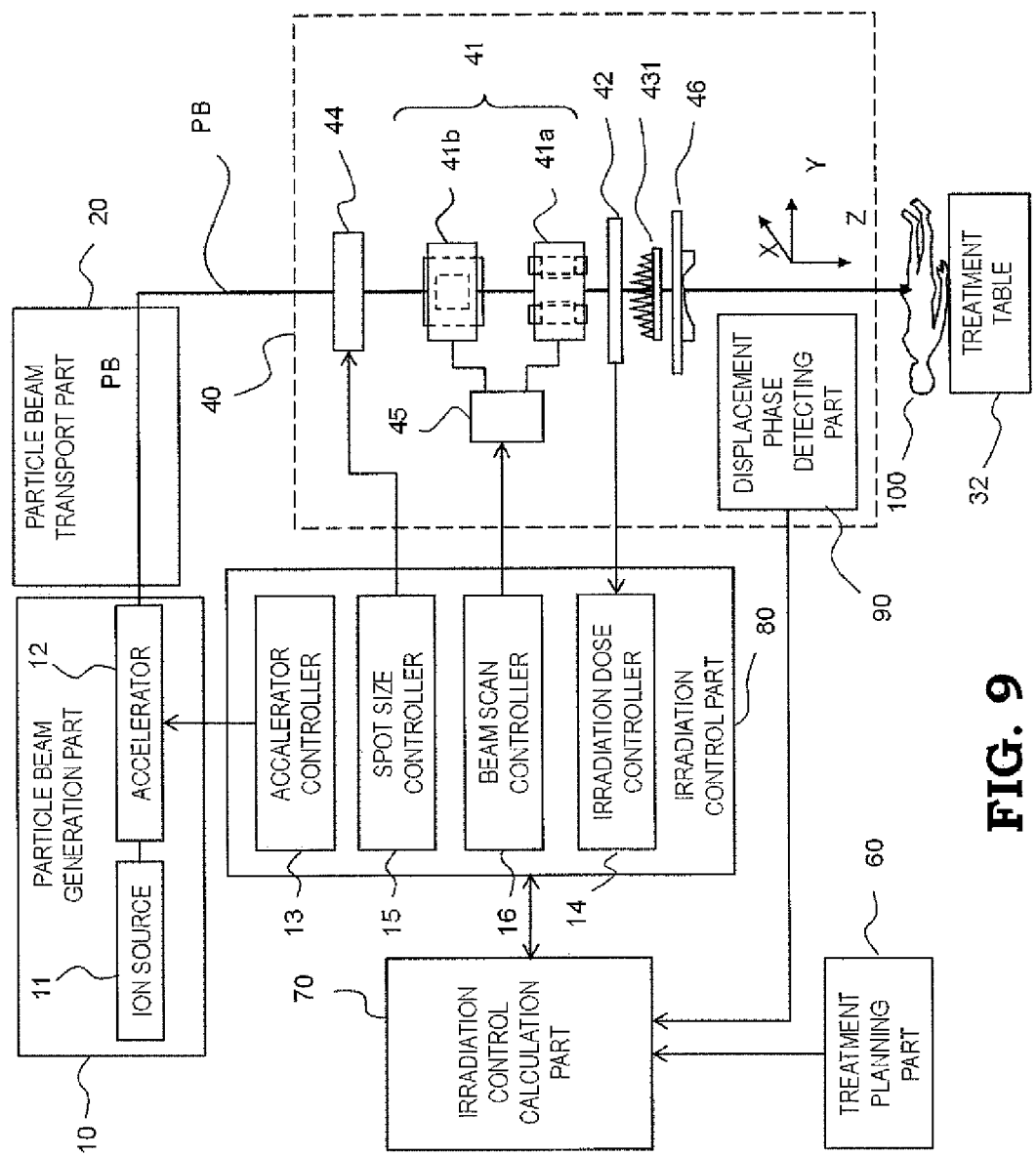
FIG. 9 is a block diagram showing an outline of configuration of a particle beam irradiation system according to EMBODIMENT 3 of the present invention.

FIG. 9 is a block diagram showing an outline of configuration of a particle beam irradiation system according to EMBODIMENT 3 of the present invention. In FIG. 9, the same symbol as that of FIG. 3 and FIG. 6 indicates the same part or a corresponding part. In EMBODIMENT 1 and EMBODIMENT 2, a SOBP is formed to have a predetermined width in a depth direction by a ridge filter 43. However, there are various shapes of an affected site. Therefore, scope of applications is limited when a SOBP having a constant width in a depth direction is formed. In EMBODIMENT 3, as shown in FIG. 9, a cone ridge filter 431 and a bolus 46 are used as an energy width expanding device. The cone ridge filter 431 is formed by arranging a large number of cones having an extremely thin shape in an XY phase which is perpendicular to a travelling direction of a beam so as for the travelling direction of a beam (z direction) to be an axis. As conceptually shown in FIG. 9, for example, by changing a height of a cone, impact which is received by a particle beam which passes through the cone ridge filter is different depending on a part of an XY plane, and a particle beam having a different energy width depending on a position can be irradiated to an irradiation target.

Figure 10:
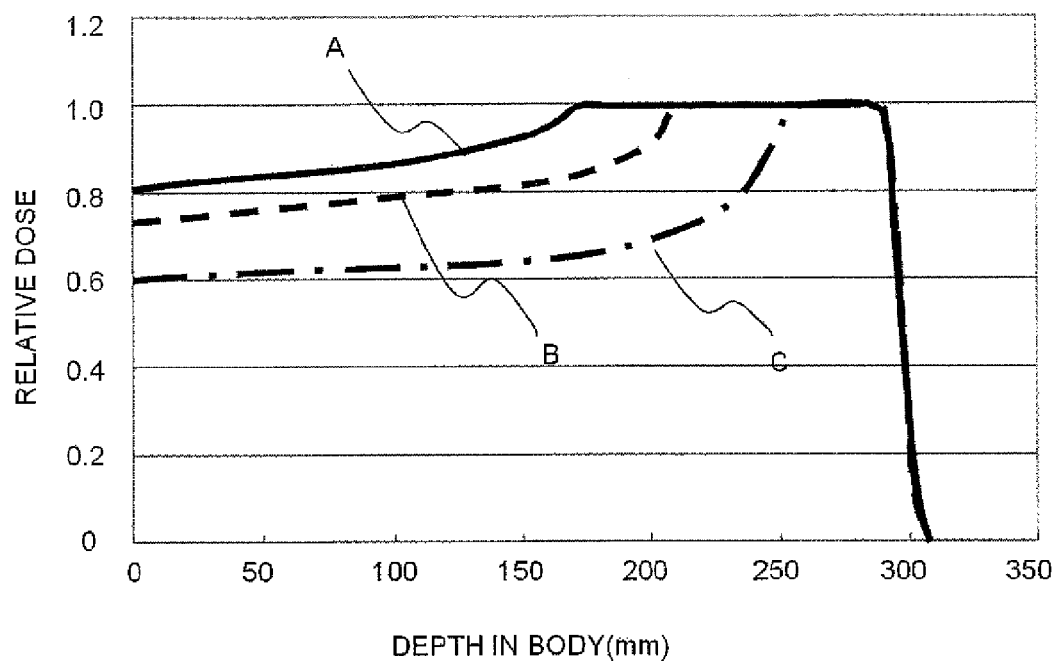
FIG. 10 is a first diagrammatic view showing an example of SOBP which is expanded by a particle beam irradiation system according to EMBODIMENT 3 of the present invention.

FIG. 10 shows an example of a SOBP which is formed by a particle beam which has passed the cone ridge filter 431. In FIG. 10, a solid line indicated by A shows a SOBP which is formed by a particle beam which has passed the cone ridge filter 431, in a case where a particle beam passes a part at which a cone having a high height is arranged (for example, a central part). Therefore, the SOBP has a wide width. A broken line indicated by B shows a SOBP which is formed by a particle beam which has passed the cone ridge filter 431 in a case where a particle beam passes a part at which a cone whose height is lower than a part which is indicated by a curve line of A is arranged (for example, the surrounding area of a central part). Therefore, the SOBP has a width which is narrower than A. A curve line of alternate long and short dash line indicated by C shows a SOBP which is formed by a particle beam which has passed the cone ridge filter 431 in a case where a particle beam passes a part at which a cone whose height is lower than that is arranged at a part which is indicated by a curve line of B (for example, the surrounding area). Therefore, the SOBP has a width which is much narrower than B. As above mentioned, a width of a SOBP is different depending on a height of a cone which is arranged. The larger a width of a SOBP, the larger necessary irradiation dose (number of irradiation particle) for obtaining an equal amount of dose at the center of a SOBP. Therefore, irradiation dose should be controlled corresponding to arrangement of a cone ridge filter. As above mentioned, scanning irradiation is most appropriate irradiation method as a method to adjust an irradiation dose corresponding to arrangement of a cone ridge filter.

Figure 11:
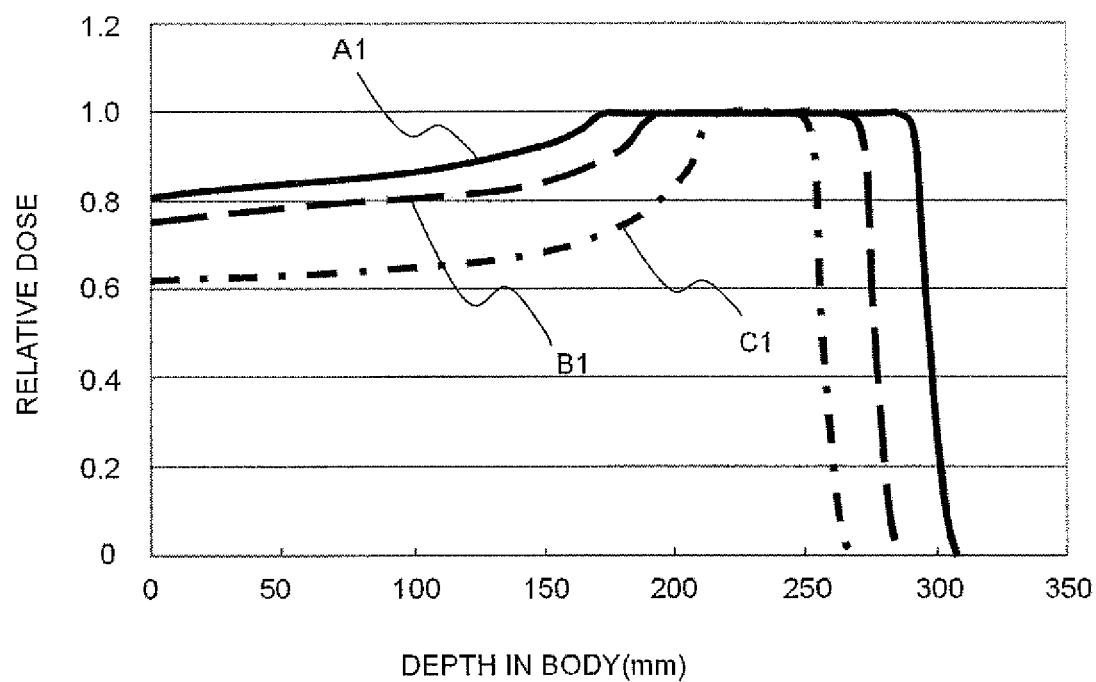
FIG. 11 is a second diagrammatic view showing an example of SOBP which is expanded by a particle beam irradiation system according to EMBODIMENT 3 of the present invention.

A particle beam which has passed the cone ridge filter 431 passes the bolus 46. A bolus is a limiter formed of a resin or the like. An energy of a particle beam which passes a bolus is limited so as to limit a range of a particle beam corresponding to a depth shape of an irradiation target. When a particle beam whose energy width is expanded by the cone ridge filter 431 as shown in FIG. 10 passes the bolus 46, it becomes a particle beam which forms a SOBP having a depth direction shown in FIG. 11. That is, for example, a particle beam which has passed a central part indicated by a curve line A in FIG. 10 also passes through a central part of the bolus 46, therefore, an energy is not limited so much. Consequently, a SOBP having a wide width and reaching a depth up to 300 mm, as shown by a curve line indicated by a solid line A1 in FIG. 11, is formed. Further, energy of a particle beam which has passed through a surrounding area of a central part shown by a curve line B in FIG. 10 is limited by the bolus 46. Therefore, as shown by a curve line indicated by a broken line B1 in FIG. 11, a SOBP having a slightly narrow width and reaching a depth limited up to 270 mm is formed. Further, energy of a particle beam which has passed through a surrounding area shown by a curve line C in FIG. 10 is limited significantly by the bolus 46. Therefore, as shown by a curve line indicated by a broken line C1 in FIG. 11, a SOBP having a narrow width and reaching a depth limited up to approximately 250 mm is formed. As above mentioned, by using the cone ridge filter 431, which have a distribution in an XY plane, and the bolus 46, an irradiation area which has a distribution in a depth direction of an irradiation target can be formed.

Figure 12:
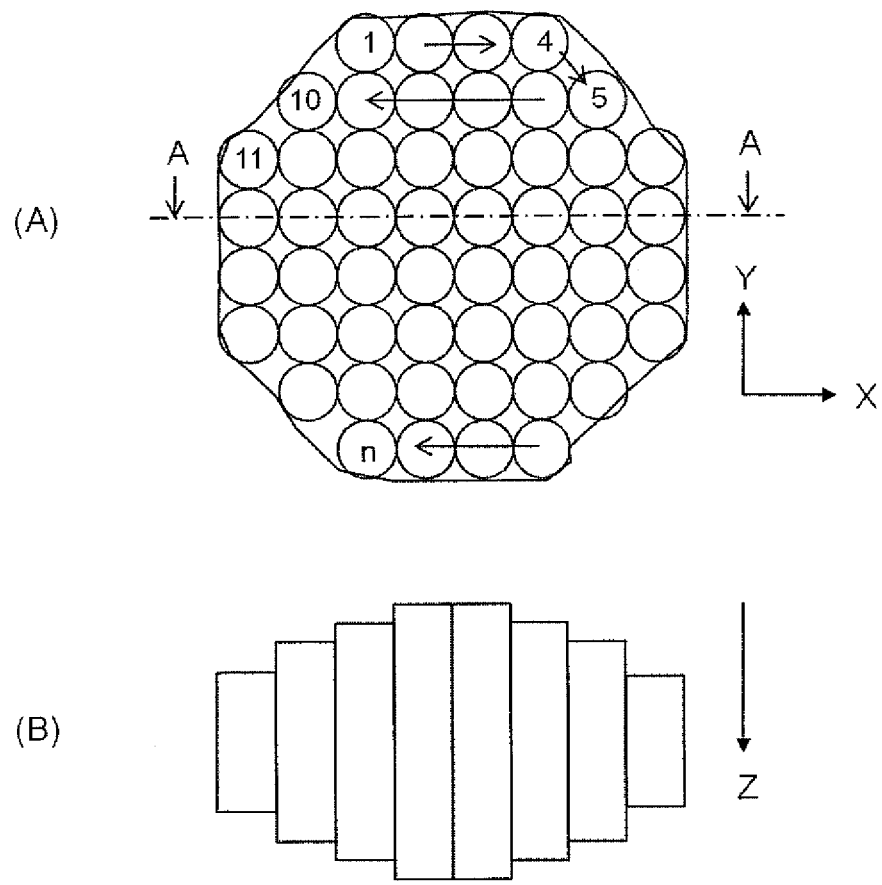
FIG. 12 is a diagram for describing an irradiation area of particle beam irradiation system according to EMBODIMENT 3 of the present invention.

FIG. 12 shows an image of an irradiation area which is formed in a case where a scanning irradiation is performed in which an XY phase is scanned by a particle beam irradiation system shown in FIG. 9. In the same way as that in FIG. 1 (A), a circle in FIG. 12 (A) shows each irradiation spot, and the numeral in a circle shows the order of scanning. Further, FIG. 12 (B) is a cross sectional view taken along the line A-A of FIG. 12 (A). As shown in FIG. 12 (B), an irradiation area in a depth direction at each irradiation spot is changed depending on a position. It can be understood such that an irradiation area in a depth direction can be made to be an area which matches a shape of an irradiation target.

In the same way as that described in Embodiment 2, in Embodiment 3, an affected site's movement period is evaluated, and irradiation can be performed by setting an irradiation parameter so as for all irradiation spots to be irradiated within one gate. Consequently, irradiation of an irradiation target in a depth direction can be realized without changing energy of a particle beam and irradiation of all irradiation spots within one gate can be completed. As a result, irradiation, in which movement of an irradiation target while irradiation is suppressed to the minimum, can be performed, and irradiation having extremely high accuracy can be realized.

Embodiment 4

Figure 13:
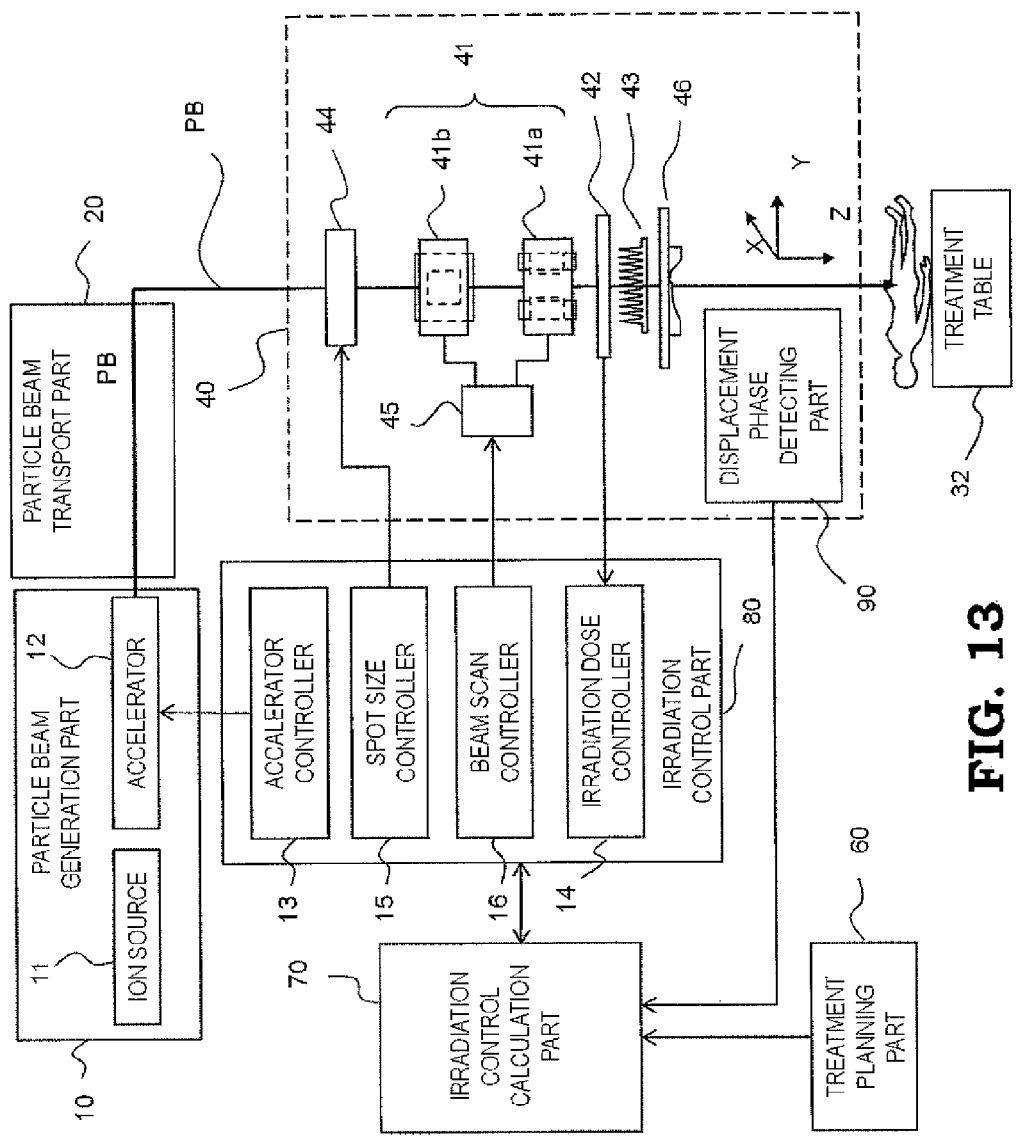
FIG. 13 is a block diagram showing an outline of configuration of a particle beam irradiation system according to EMBODIMENT 4 of the present invention.

FIG. 13 is a block diagram showing an outline of configuration of a particle beam irradiation system according to EMBODIMENT 4 of the present invention. In FIG. 13, the same symbol as that of FIG. 3, FIG. 6 and FIG. 9 indicates the same part or a corresponding part. Various configurations can be used to form a predetermined irradiation area in a depth direction without changing energy of a particle beam, that is, to form a SOBP. In FIG. 13, the configuration is such that a ridge filter 43 and a bolus 46 are used so as to form an irradiation area in a depth direction. Further, in order to form an irradiation area which matches a shape of an irradiation target in a lateral direction, a collimator such as a multi-leaf collimator (MLC) or a patient collimator may be used.

In conventional scanning irradiation methods, an irradiation area in a depth direction is irradiated by changing energy of a particle beam so as to form a different irradiation area in a depth direction. On the other hand, according to this invention, the configuration is such that an irradiation area is formed along whole area of an irradiation target in a depth direction by using an energy width expanding device such as a ridge filter which is provided at the downstream of a deflection electromagnet for scanning 41, and a bolus which is an energy limiter. According to the above-mentioned configuration, by forming an irradiation area in a lateral direction by a scanning irradiation in which an irradiation spot is scanned, irradiation of whole area of an irradiation target can be completed within one gate, for example. Consequently, irradiation having high accuracy can be realized.

Embodiment 5

Figure 14:
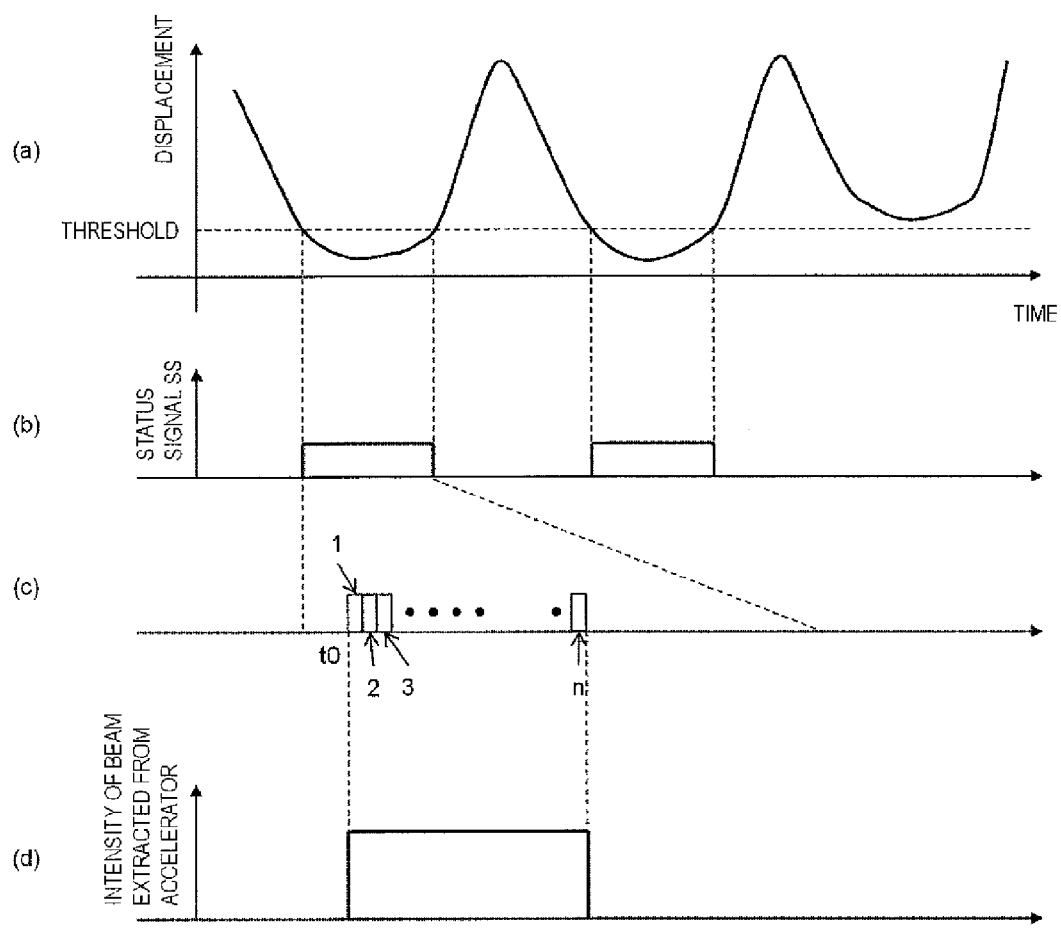
FIG. 14 is a diagrammatic view for explaining an operation of a particle beam irradiation system according to EMBODIMENT 5 of the present invention.
Figure 15:
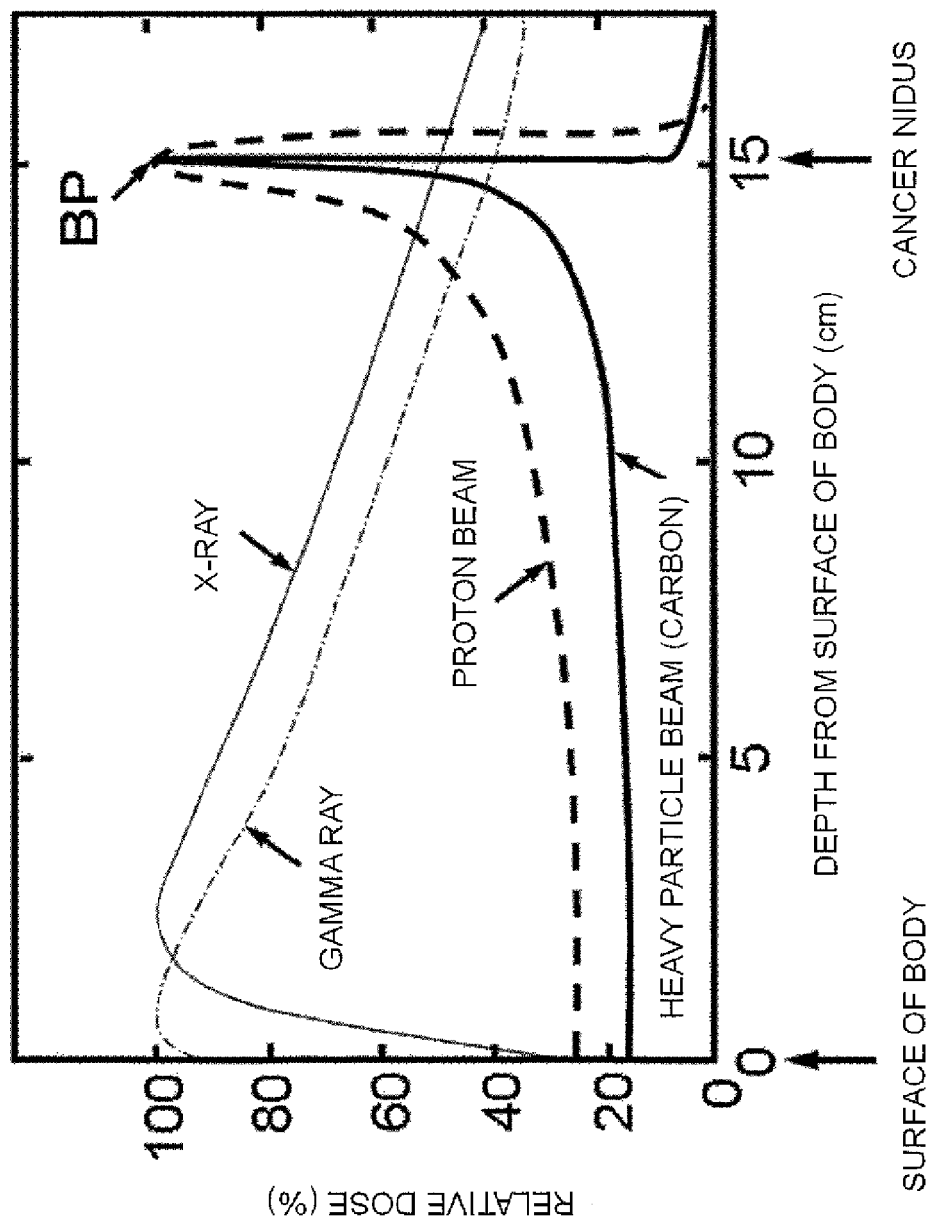
FIG. 15 is a diagram showing a dose distribution of radiation inside a body in a case where a human body is irradiated with various kinds of radiation.

FIG. 14 is a diagrammatic view for explaining an operation of a particle beam irradiation system according to EMBODIMENT 5 of the present invention. FIGS. 14 (a), (b) and (c) are similar to FIGS. 8 (a), (b) and (c), respectively. FIG. 14 (d) shows a time change of an intensity of a beam which is extracted from an accelerator 12, corresponding to an enlarged time axis in FIG. 14(c), and shows the state where a particle beam is extracted from the accelerator. For example, in EMBODIMENT 2, whole irradiation area is irradiated within one gate. On the other hand, an operation of a particle beam irradiation system according to EMBODIMENT 5 is such that the timing in which a particle beam is extracted from an accelerator is in synchronization with the timing of irradiation.

First, at the irradiation start time t0 within a gate, a remaining time for capable of irradiation is computed, when a remaining time for capable of irradiation does not satisfy the planned irradiation time, an extraction will be suspended. When a remaining time for capable of irradiation satisfies the planned irradiation time, an extraction will be performed. By evaluating a moving period of an affected site and an operation period of an accelerator, irradiation of whole irradiation area within one gate can be completed. When irradiation is performed in a plurality of gates, in a case where there is a variation in a position during a move period of an affected site, a high dose area of dose distribution or a low dose area of dose distribution which is not planned is generated in principle. When irradiation of whole irradiation area can be completed within one gate, the accuracy of dose distribution can be increased.

DESCRIPTION OF THE REFERENCE NUMERALS

10: particle beam generation part
11: injector
12: accelerator
13: accelerator controller
14: irradiation dose controller
15: spot size controller
16: beam scan controller
20: particle beam transport part
30, 30A, 30B: particle beam irradiation part
32: treatment table
40: irradiation nozzle
41, 41a, 41b: deflection electromagnet for scanning
42: dose monitor
43: ridge filter (energy width expanding device)
431: cone ridge filter (energy width expanding device)
44: beam diameter changer
60: treatment planning part
70: irradiation control calculation part
80: irradiation control part
90: displacement phase detecting part
PB: particle beam

The invention claimed is:

1. A particle beam irradiation system comprising:
a particle beam generation part, at which an accelerator is provided, configured to generate a particle beam;
an irradiation nozzle configured to irradiate the particle beam to an irradiation target;
a displacement phase detecting part which detects a phase of a displacement of the irradiation target, wherein the displacement phase detecting part outputs a gate signal which permits irradiation of the particle beam onto the irradiation target while the phase of displacement of the irradiation target is in a predetermined phase; and
an irradiation control part configured to control the irradiating particle beam,
wherein the irradiation nozzle comprises:
(i) deflection electromagnets configured to deflect the particle beam in two dimensions in the lateral direction, which is perpendicular to an irradiation direction of the particle beam, and
(ii) an energy width expanding device through which the particle beam passes so as to expand an energy width of the particle beam and form a spread out Bragg Peak (SOBP) in a depth direction of the irradiation target, said energy width expanding device being configured to form the SOBP in the depth direction along a whole irradiation area in the depth direction of the irradiation target without changing an energy of the particle beam entering said energy width expanding device during irradiation, and
wherein the irradiation control part
(i) controls the deflection electromagnets to scan the irradiation target with the particle beam by moving an irradiation spot within the irradiation target in a stepwise manner in a lateral direction along the whole irradiation area of the irradiation target while one gate signal, among a plurality of gate signals, is outputted from the displacement phase detecting part, and (ii) controls the accelerator to start extracting the particle beam when the irradiation control part determines that a computed remaining time, in which the system is capable of extracting the particle beam from the accelerator, is longer than a planned irradiation time within the one gate signal.

2. The particle beam irradiation system as claimed in claim 1 further comprising:

a treatment planning part; and an irradiation control calculation part which computes an irradiation parameter of each irradiation spot of the irradiation spots which move stepwise by using data which is received from the treatment planning part, wherein the irradiation control calculation part (i) evaluates a phase of a moving period of the irradiation target by using data which is received from the displacement phase detecting part, and (ii) computes the irradiation parameter for irradiating the whole irradiation area in a lateral direction of the irradiation target while the one gate signal is outputted so as to transmit data for irradiating by the computed irradiation parameter.

3. The particle beam irradiation system as claimed in claim 1, wherein the energy width expanding device is an element which expands an energy width to have different distributions in the lateral direction.

* * * * *